(12) United States Patent
Hong et al.

(10) Patent No.: US 11,603,521 B2
(45) Date of Patent: Mar. 14, 2023

(54) AMINO ACID DEHYDROGENASE MUTANT AND USE THEREOF

(71) Applicant: ASYMCHEM LIFE SCIENCE (TIANJIN) CO., LTD, Tianjin (CN)

(72) Inventors: Hao Hong, Morrisville, NC (US); Gage James, Morrisville, NC (US); Jiangping Lu, Tianjin (CN); Na Zhang, Tianjin (CN); Xuecheng Jiao, Tianjin (CN); Rui Li, Tianjin (CN); Kejian Zhang, Tianjin (CN); Yu Zhang, Tianjin (CN); Yiming Yang, Tianjin (CN)

(73) Assignee: ASYMCHEM LIFE SCIENCE (TIANJIN) CO., LTD, Tianjin (CN)

( * ) Notice: Subject to any disclaimer, the term of this patent is extended or adjusted under 35 U.S.C. 154(b) by 0 days.

(21) Appl. No.: 17/266,461

(22) PCT Filed: Aug. 17, 2018

(86) PCT No.: PCT/CN2018/101132
§ 371 (c)(1),
(2) Date: Feb. 5, 2021

(87) PCT Pub. No.: WO2020/034209
PCT Pub. Date: Feb. 20, 2020

(65) Prior Publication Data
US 2021/0292717 A1    Sep. 23, 2021

(51) Int. Cl.
| C12N 9/06 | (2006.01) |
| C12N 15/70 | (2006.01) |
| C12P 13/04 | (2006.01) |
| C12R 1/19 | (2006.01) |

(52) U.S. Cl.
CPC .......... *C12N 9/0012* (2013.01); *C12N 15/70* (2013.01); *C12P 13/04* (2013.01); *C12R 2001/19* (2021.05); *C12Y 104/99001* (2013.01)

(58) Field of Classification Search
None
See application file for complete search history.

(56) References Cited

U.S. PATENT DOCUMENTS

| 2016/0348079 A1 | 12/2016 | Kim et al. | |
| 2020/0248153 A1* | 8/2020 | Akita | C12N 9/0014 |

FOREIGN PATENT DOCUMENTS

| CN | 105821014 A | 8/2016 |
| JP | 2017108740 | 6/2017 |
| WO | 2019031574 | 2/2019 |

OTHER PUBLICATIONS

Bornscheuer et al. Curr Protoc Protein Sci. Nov. 2011;Chapter 26:Unit26.7. (Year: 2011).*
Yoshikuni et al. Curr Opin Chem Biol. Apr. 2007;11(2):233-9. (Year: 2007).*
Accession A0A1M5M5H3. Mar. 15, 2017 (Year: 2017).*
GenBank Accession No. WP_073090506, dated Dec. 18, 2016; https://www.ncbi.nlm.nih.gov/protein/WP_073090506.1.
Akita et al., 2020, "Characterization of an NAD(P)+-dependent meso-diaminopimelate dehydrogenase from Thermosyntropha lipolytica", Biochimica Et Biophysica Acta (BBA)—Proteins & Proteomics, 1868:140476.
Cheng et al., 2018, "Gene Mining. Directed Engineering of Amino Acid Dehydrogenases and Its Application in Synthesis of Chiral Amino Acid"; China Master's Theses Full-Text Database, Engineering Science & Technology 1, 20-43.
Database UniProt [Online] Mar. 15, 2017, entry version: Jun. 2, 2021, retrieved from EBI accession No. Uniprot:AOA1 M5M5H3 Database accession No. AOA1 M5M5H3.
Extended European Search Report for EP 18930079 dated Feb. 11, 2022.
Gao et al., 2013, "Engineering the meso-Diaminopimelate Dehydrogenase from Symbiobacterium thermophilum by Site Saturation Mutagenesis for D-Phenylalanine Synthesis", Applied and Envi Ron Mental Microbiology, 79:5078-5081.
Gao et al., 2017, "A Newly Determined Member of the meso-Diaminopimelate Dehydrogenase Family with a Broad Substrate Spectrum", Applied and Environmental Microbiology, 83:1-10.
Office Action for JP 2020569982.

* cited by examiner

*Primary Examiner* — Christian L Fronda
(74) *Attorney, Agent, or Firm* — Riverside Law LLP

(57) ABSTRACT

Provided is an amino acid dehydrogenase mutant. The amino acid sequence of the mutant is obtained by mutating the amino acid sequence shown in SEQ ID NO:1. The mutation includes at least one of the following mutation sites: 64th, 94th, 133rd, 137th, 148th, 168th, 173rd, 183 rd, 191st, 207th, 229th, 248th, 255th and 282nd sites; or the amino acid sequence of the amino acid dehydrogenase mutant is an amino acid sequence having the mutation sites in the mutated amino acid sequence and having a 80% or more homology with the mutated amino acid sequence. The mutant enzyme activity is more than 50 times higher than that of wild amino acid dehydrogenase, and the enzyme specificity is also correspondingly improved.

1 Claim, No Drawings

Specification includes a Sequence Listing.

SEQUENCE LISTING

```
<160> NUMBER OF SEQ ID NOS: 2

<210> SEQ ID NO 1
<211> LENGTH: 301
<212> TYPE: PRT
<213> ORGANISM: artificial sequence
<220> FEATURE:
<223> OTHER INFORMATION: amino acid dehydrogenase

<400> SEQUENCE: 1

Met Gly Glu Lys Ile Arg Val Ala Ile Val Gly Tyr Gly Asn Ile Gly
1               5                   10                  15

Arg Tyr Ala Leu Asp Ala Ile Lys Ala Ala Pro Asp Met Glu Leu Ala
            20                  25                  30

Gly Val Val Arg Arg Ser Ser Leu Gly Asp Lys Pro Ala Glu Leu
        35                  40                  45

Ala Asp Val Pro Val Val Gly Ser Ile Lys Glu Leu Thr Gly Val Lys
    50                  55                  60

Val Ala Leu Leu Cys Thr Pro Thr Arg Ser Val Pro Glu Tyr Ala Arg
65                  70                  75                  80

Glu Ile Leu Ala Leu Gly Ile Asn Thr Val Asp Ser Tyr Asp Ile His
                85                  90                  95

Gly Gln Leu Ala Asp Leu Arg Leu Glu Leu Asp Lys Val Ala Lys Glu
            100                 105                 110

His Asn Ala Val Ala Val Ile Ser Ala Gly Trp Asp Pro Gly Thr Asp
        115                 120                 125

Ser Met Val Arg Cys Met Phe Glu Phe Met Ala Pro Lys Gly Ile Thr
    130                 135                 140
```

Tyr Thr Asn Phe Gly Pro Gly Met Ser Met Gly His Ser Val Ala Val
145                 150                 155                 160

Lys Ala Val Lys Gly Val Lys Asn Ala Leu Ser Met Thr Ile Pro Leu
            165                 170                 175

Gly Thr Gly Val His Arg Arg Met Val Tyr Val Glu Leu Glu Pro Gly
        180                 185                 190

Ala Asp Phe Ala Gln Val Glu Lys Ala Val Lys Thr Asp Pro Tyr Phe
            195                 200                 205

Val Lys Asp Glu Thr His Val Ile Gln Val Glu Asp Val Asp Ala Leu
        210                 215                 220

Ile Asp Met Gly His Gly Val Leu Met Glu Arg Lys Gly Val Ser Gly
225                 230                 235                 240

Gly Thr His Asn Gln Leu Leu Ser Phe Ser Met Arg Ile Asn Asn Pro
                245                 250                 255

Ala Leu Thr Ala Gln Ile Met Val Ala Ser Arg Ala Ser Val Lys
            260                 265                 270

Gln Lys Pro Gly Ala Tyr Thr Met Ile Gln Ile Pro Ile Ile Asp Tyr
        275                 280                 285

Met Tyr Gly Asp Pro Asp Glu Ile Ile Arg Gln Leu Val
    290                 295                 300

<210> SEQ ID NO 2
<211> LENGTH: 906
<212> TYPE: DNA
<213> ORGANISM: artificial sequence
<220> FEATURE:
<223> OTHER INFORMATION: amino acid dehydrogenase gene

<400> SEQUENCE: 2

| | | |
|---|---|---|
| atgggtgaaa aaattcgcgt tgcaatcgtt ggttacggca acattggccg ttatgccctg | 60 |
| gatgcaatca agccgcacc ggatatggaa ctggccggcg tggtgcgccg tagtagcagt | 120 |
| ctgggcgaca agccggccga actggcagat gtgcctgttg tgggcagcat caaagagctg | 180 |
| accggtgtga agttgcact gctgtgcacc ccgacccgca gtgttccgga atatgcccgt | 240 |
| gagattctgg ccctgggcat caacaccgtg gatagctatg acatccacgg tcagctggcc | 300 |
| gatctgcgtc tggagctgga taaagtggcc aaagaacaca cgccgtggcc cgtgattagc | 360 |
| gcaggttggg accctggcac cgatagcatg gttcgctgca tgttcgagtt tatggccccg | 420 |
| aagggcatca cctataccaa tttcggtccg ggcatgagca tgggtcacag cgtggccgtt | 480 |
| aaagccgtga agggcgtgaa aaatgccctg agcatgacca ttccgctggg caccggtgtt | 540 |
| catcgtcgta tggtgtatgt ggagctggaa cctggtgccg atttcgccca ggtggaaaag | 600 |
| gccgtgaaaa ccgatccgta cttcgtgaag gatgagaccc acgtgattca ggtggaagac | 660 |
| gtggacgccc tgattgatat gggccatggc gttctgatgg aacgtaaggg cgttagcggt | 720 |
| ggcacccata accagctgct gagcttcagt atgcgtatca taacccggcc ctgaccgcc | 780 |
| cagattatgg tggccagcgc ccgtgccagc gtgaaacaga accgggcgc atacaccatg | 840 |
| atccagattc cgatcattga ttacatgtac ggcgacccgg atgagatcat cgtcagctg | 900 |
| gtgtaa | 906 |

AMINO ACID DEHYDROGENASE MUTANT AND USE THEREOF

CROSS-REFERENCE TO RELATED APPLICATIONS

This application is the U.S. national phase application filed under 35 U.S.C. § 371 claiming benefit to International Patent Application No. PCT/CN2018/101132, filed on Aug. 17, 2018, the disclosure of which is incorporated herein by reference in its entirety.

TECHNICAL FIELD

The present disclosure relates to the field of biotechnology, and in particular to an amino acid dehydrogenase mutant and use thereof.

BACKGROUND

Amino acids are amphoteric compounds having one carboxyl and one amino at least, and may be classified into two categories in accordance with existing ways of the amino acids, that is, natural amino acids and unnatural amino acids. The natural amino acids are amino acids that exist in nature, while the unnatural amino acids are synthetic amino acids. Generally, some groups are introduced into side chains of the natural amino acids so as to optimize their properties. Due to special structural properties, the amino acids and derivatives thereof have wide applications in aspects such as agriculture, industry, chemical engineering, food and medicine. Optically active unnatural amino acids are chiral synthesis units of some bioactive peptides, and are also important intermediates of many medicines and fine chemicals.

With in-depth scientific researches and the development of new drugs, D-amino acids become more and more important in medicinal development and preparation and food fields.

During enzymatic synthesis of the D-amino acids, used enzymes mainly include transaminase (*Appl. Microbiol. Blot.* 2008, 79, 775-784) and amino acid dehydrogenase (*Journal of the American Chemical Society,* 2006, 128 (33):10923-10929). By taking prochiral ketonic acid as a substrate and utilizing free $NH_4^+$ as an amino donor, the amino acid dehydrogenase can be used for synthesizing chiral amino acids in the presence of a co-enzyme cycle system, and the synthesis method is green and economic.

However, D-amino acid dehydrogenase existing in nature is very limited in substrate spectrum, and has extremely low reaction activity on most of the substrates, particularly substrates having higher steric hindrance. The concentration of the substrate is low in the reaction; loads on the enzyme are quite high; and cost is higher. Generally speaking, wild enzymes should be modified by the mean of orthogenesis, and various properties of the enzymes are increased, so that the enzymes can be applied to production.

SUMMARY

A purpose of the present disclosure is to provide an amino acid dehydrogenase mutant and use thereof, for solving a technical problem in the prior art that wild amino acid dehydrogenase is unsuitable for industrial production.

To achieve the above purpose, according to one aspect of the present disclosure, an amino acid dehydrogenase mutant is provided. The amino acid sequence of the mutant is obtained by mutating the amino acid sequence shown in SEQ ID NO:1; the mutation includes at least one of the following mutation sites: 64th, 94th, 133rd, 137th, 148th, 168th, 173rd, 183rd, 191st, 207th, 229th, 248th, 255th and 282nd sites; lysine at the 64th site is mutated into aspartic acid; aspartic acid at the 94th site is mutated into alanine, glycine, valine or serine; cysteine at the 133rd site is mutated into alanine or threonine; phenylalanine at the 137th site is mutated into alanine; phenylalanine at the 148th site is mutated into valine or alanine; asparaginate at the site 168 is mutated into aspartic acid; threonine at the 173rd site is mutated into serine, histidine, tryptophan, phenylalanine or leucine; arginine at the 183rd site is mutated into phenylalanine, lysine, cysteine, valine, alanine or leucine; proline at the 191st site is mutated into glutamic acid; tyrosine at the 207th site is mutated into arginine, glutamic acid, phenylalanine or valine; histidine at the 229th site is mutated into valine, alanine, glycine, asparaginate, serine or threonine; serine at the 248th site is mutated into glutamic acid; asparaginate at the 255th site is mutated into alanine, glutamine or aspartic acid; glutamine at the 282nd site is mutated into glutamic acid; or the amino acid sequence of the amino acid dehydrogenase mutant has the mutation sites in the mutated amino acid sequence, and has more than 80% homology with the mutated amino acid sequence.

Further, the mutation at least includes one of the following mutation sites: lysine at the 64th site is mutated into aspartic acid; aspartic acid at the 94th site is mutated into serine; cysteine at the 133rd site is mutated into threonine; phenylalanine at the 137th site is mutated into alanine; phenylalanine at the 148th site is mutated into valine; threonine at the 173rd site is mutated into phenylalanine; arginine at the 183rd site is mutated into phenylalanine, lysine, cysteine, valine or leucine; proline at the 191st site is mutated into glutamic acid; and histidine at the 229th site is mutated into valine, alanine, glycine, serine or threonine.

Preferably, the mutation at least includes one of the following mutation sites: arginine at the 183rd site is mutated into cysteine and histidine at the 229th site is mutated into serine; arginine at the 183rd site is mutated into valine and histidine at the 229th site is mutated into serine; arginine at the 183rd site is mutated into leucine and histidine at the 229th site is mutated into alanine; threonine at the 173rd site is mutated into phenylalanine and arginine at the 183rd site is mutated into cysteine; arginine at the 183rd site is mutated into cysteine and histidine at the 229th site is mutated into leucine; arginine at the 183rd site is mutated into cysteine and tyrosine at the 207th site is mutated into arginine; arginine at the 183rd site is mutated into alanine and histidine at the 229th site is mutated into serine; arginine at the 183rd site is mutated into valine and histidine at the 229th site is mutated into asparaginate; and threonine at the 173rd site is mutated into histidine and histidine at the 229th site is mutated into serine.

Preferably, the mutation at least includes one of the following mutation sites: arginine at the 183rd site is mutated into cysteine, histidine at the 229th site is mutated into serine and phenylalanine at the 148th site is mutated into alanine; arginine at the 183rd site is mutated into cysteine, histidine at the 229th site is mutated into serine and tyrosine at the 207th site is mutated into arginine; arginine at the 183rd site is mutated into cysteine, histidine at the 229th site is mutated into serine and phenylalanine at the 148th site is mutated into valine; arginine at the 183rd site is mutated into cysteine, histidine at the 229th site is mutated into serine and threonine at the 173rd site is mutated into phenylalanine; arginine at the 183rd site is mutated into cysteine, histidine at the 229th site is mutated into serine and threonine at the 173rd site is mutated into tryptophan; arginine at the 183rd site is mutated into cysteine, histidine at the 229th site is mutated into serine and tyrosine at the 207th site is mutated into glutamic acid; arginine at the 183rd site is mutated into cysteine, histidine at the 229th site is mutated into serine and tyrosine at the 207th site is mutated into arginine; arginine at the 183rd site is mutated into alanine, histidine at the 229th site is mutated into serine and threonine at the 173rd site is mutated into histidine; arginine at the 183rd site is mutated into valine, histidine at the 229th site is mutated into serine and threonine at the 173rd site is mutated into histidine; arginine at the 183rd site is mutated into valine, histidine at the 229th site is mutated into serine and phenylalanine at the 148th site is mutated into alanine; threonine at the 173rd site is mutated into histidine, histidine at the 229th site is mutated into serine and phenylalanine at the 148th site is mutated into alanine;

or the amino acid sequence of the amino acid dehydrogenase mutant has the mutation sites in the mutated amino acid sequence, and has more than 95% homology with the mutated amino acid sequence.

According to another aspect of the present disclosure, a DNA molecule is provided. The DNA molecule encodes any one of the above amino acid dehydrogenase mutants.

According to another aspect of the present disclosure, a recombinant plasmid is provided. The recombinant plasmid includes any of the above DNA molecules.

Further, the recombinant plasmid is pET-22b(+), pET-22b (+), pET-3a(+), pET-3d(+), pET-11a(+), pET-12a(+), pET-14b(+), pET-15b(+), pET-16b(+), pET-17b(+), pET-19b(+), pET-20b(+), pET-21a(+), pET-23a(+), pET-23b(+), pET-24a (+), pET-25b(+), pET-26b(+), pET-27b(+), pET-28a(+), pET-29a(+), pET-30a(+), pET-31b(+), pET-32a(+), pET-35b (+), pET-38b(+), pET-39b(+), pET-40b(+), pET-41a(+), pET-41b(+), pET-42a(+), pET-43a(+), pET-43b(+), pET-44a (+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19.

According to another aspect of the present disclosure, a host cell is provided. The host cell includes any of the recombinant plasmids above.

Further, the host cell contains a prokaryotic cell, a yeast or an eukaryotic cell; preferably, the prokaryotic cell is an *Escherichia coli* BL21 cell or an *Escherichia coli* DH5a competent cell.

According to another aspect of the present disclosure, a method for producing D-amino acids is provided. The method includes a step of carrying out a catalytic reductive amination reaction on a ketone compound by using amino acid dehydrogenase, wherein the amino acid dehydrogenase is any of the above amino acid dehydrogenase mutants.

Further, the ketone compound is

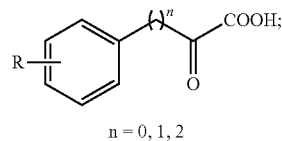

$n = 0, 1, 2$ and a reductive amination reaction product is

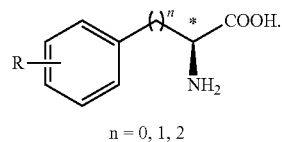

$n = 0, 1, 2$

Further, an amino donor in the reductive amination reaction is ammonium chloride.

The above amino acid dehydrogenase mutant of the present disclosure is obtained by mutating the amino acid dehydrogenase as shown in SEQ ID NO:1 through a method of site-directed mutation and through a method of directed screening, thereby changing the amino acid sequence thereof, realizing a change of protein structure and function. The amino acid dehydrogenase mutant of the present disclosure has an advantage of greatly improving enzymatic activity; the enzymatic activity is increased by over 50 times compared with that of the wild amino acid dehydrogenase; and the enzyme specificity is correspondingly increased, thereby the cost in industrial production of the D-amino acids is greatly reduced.

DETAILED DESCRIPTION OF THE EMBODIMENTS

It should be noted that the embodiments in this disclosure and the features of the embodiments can be combined with each other if no conflict is caused. The present disclosure will be described in detail below in combination with the embodiments.

Activity and stability of the following amino acid dehydrogenase shown as SEQ ID NO:1 are increased by the inventor of the present disclosure by an orthogenesis method:

(MGEKIRVAIVGYGNIGRYALDAIKAAPDMELAGWRRSSSLGDKPAELADVPVV

GSIKELTGVKVALLCTPTRSVPEYAREILALGINTVDSYDIHGQLADLRLELDKVAKEH

NAVAVISAGWDPGTDSMVRCMFEFMAPKGITYTNFGPGMSMGHSVAVKAVKGVKN

ALSMTIPLGTGVHRRMVYVELEPGADFAQVEKAVKTDPYFVKDETHVIQVEDVDALI

DMGHGVLMERKGVSGGTHNQLLSFSMRINNPALTAQIMVASARASVKQKPGAYTMI

QIPIIDYMYGDPDEIIRQLV, a corresponding nucleotide sequence
 SEQ ID NO: 2:

ATGGGTGAAAAAATTCGCGTTGCAATCGTTGGTTACGGCAACATTGGCCGTTATG

CCCTGGATGCAATCAAAGCCGCACCGGATATGGAACTGGCCGGCGTGGTGCGC

CGTAGTAGCAGTCTGGGCGACAAGCCGGCCGAACTGGCAGATGTGCCTGTTGT

-continued

```
GGGCAGCATCAAAGAGCTGACCGGTGTGAAAGTTGCACTGCTGTGCACCCCGA

CCCGCAGTGTTCCGGAATATGCCCGTGAGATTCTGGCCCTGGGCATCAACACCG

TGGATAGCTATGACATCCACGGTCAGCTGGCCGATCTGCGTCTGGAGCTGGATA

AAGTGGCCAAAGAACACAACGCCGTGGCCGTGATTAGCGCAGGTTGGGACCCT

GGCACCGATAGCATGGTTCGCTGCATGTTCGAGTTTATGGCCCCGAAGGGCATC

ACCTATACCAATTTCGGTCCGGGCATGAGCATGGGTCACAGCGTGGCCGTTAAA

GCCGTGAAGGGCGTGAAAAATGCCCTGAGCATGACCATTCCGCTGGGCACCGG

TGTTCATCGTCGTATGGTGTATGTGGAGCTGGAACCTGGTGCCGATTTCGCCCA

GGTGGAAAAGGCCGTGAAAACCGATCCGTACTTCGTGAAGGATGAGACCCACG

TGATTCAGGTGGAAGACGTGGACGCCCTGATTGATATGGGCCATGGCGTTCTGA

TGGAACGTAAGGGCGTTAGCGGTGGCACCCATAACCAGCTGCTGAGCTTCAGTA

TGCGTATCAATAACCCGGCCCTGACCGCCCAGATTATGGTGGCCAGCGCCCGTG

CCAGCGTGAAACAGAAACCGGGCGCATACACCATGATCCAGATTCCGATCATTG

ATTACATGTACGGCGACCCGGATGAGATCATTCGTCAGCTGGTGTAA),
``` thereby decreasing the dosage of enzymes. Mutation sites were introduced into the amino acid dehydrogenase shown as SEQ ID NO:1 by a whole-plasmid PCR manner; mutants were subjected to activity and stability detection; and mutants with increased activity or stability were selected.

Wild amino acid dehydrogenase shown as SEQ ID NO:1 was taken as a template; 43 pairs of site-specific mutation primers (i.e., K64D, D94A, D94G, D94V, D94S, C133A, C133T, F137A, F148V, F148A, N168D, T173S, T173F, T173H, T173W, T173L, R183F, R183K, R183L, R183C, R183V, R183A, P191E, Y207F, Y207R, Y207E, Y207V, H229V, H229A, H229N, H229G, H229S, H229T, S248E, N255A, N255Q, N255D, Q282E) were designed; and by utilizing the site-specific mutation means, by taking pET-22b (+) as an expression vector, mutation plasmids with target genes were obtained.

Herein, site-directed mutagenesis: refers to the introduction of desired changes (usually characterizing changes in favorable directions) to the target DNA fragments (either genomes or plasmids) by polymerase chain reaction (PCR), including addition, deletion, point mutation, etc. of bases. Site-directed mutagenesis can rapidly and efficiently improve the properties and characterization of target proteins expressed by DNA, and is a very useful means in gene research.

The method of introducing site-directed mutation by whole plasmid PCR is simple and effective, and is a widely used method at present. The principle is as follows, a pair of primers containing mutation sites (forward and reverse), and the template plasmid is annealed, then "cycled extended" by polymerase, the so-called cyclic extension means that the polymerase extends the primers according to the template, and then returns to the 5' end of the primers after a circle, after cycles of repeated heating and annealing, this reaction is different from rolling circle amplification, will not form multiple tandem copies. The extension products of the forward primer and the reverse primer are annealed and paired to form a nicked open circular plasmid. Dpn I digests the extension product, since the original template plasmid is derived from conventional *E. coli*, subjected to dam methylation modification and sensitive to Dpn I, it is chopped, and the plasmid with the mutant sequence synthesized in vitro is not cut due to no methylation, so that the plasmid is successfully transformed in subsequent transformation, and clone of the mutant plasmid can be obtained.

The above mutant plasmid is transformed into an *Escherichia coli* cell, and over-expressed in the *Escherichia coli*. After that, a crude enzyme is obtained through a method of ultrasonic cell-break. An optimum condition of amino acid dehydrogenase induced expression is as follows: 25° C., and inducing overnight in 0.1 mM of IPTG.

According to a typical embodiment of the present disclosure, an amino acid dehydrogenase mutant is provided. The amino acid sequence of the mutant is obtained by mutating the amino acid sequence shown in SEQ ID NO:1; the mutation includes at least one of the following mutation sites: 64th, 94th, 133rd, 137th, 148th, 168th, 173rd, 183rd, 191st, 207th, 229th, 248th, 255th and 282nd sites; lysine at the 64th site is mutated into aspartic acid; aspartic acid at the 94th site is mutated into alanine, glycine, valine or serine; cysteine at the 133rd site is mutated into alanine or threonine; phenylalanine at the 137th site is mutated into alanine; phenylalanine at the 148th site is mutated into valine or alanine; asparaginate at the site 168 is mutated into aspartic acid; threonine at the 173rd site is mutated into serine, histidine, tryptophan, phenylalanine or leucine; arginine at the 183rd site is mutated into phenylalanine, lysine, cysteine, valine, alanine or leucine; proline at the 191st site is mutated into glutamic acid; tyrosine at the 207th site is mutated into arginine, glutamic acid, phenylalanine or valine; histidine at the 229th site is mutated into valine, alanine, glycine, asparaginate, serine or threonine; serine at the 248th site is mutated into glutamic acid; asparaginate at the 255th site is mutated into alanine, glutamine or aspartic acid; glutamine at the 282nd site is mutated into glutamic acid; or the amino acid sequence of the amino acid dehydrogenase mutant has the mutation sites in the mutated amino acid sequence, and has more than 80% homology with the mutated amino acid sequence.

Preferably, the mutation at least includes one of the following mutation sites: lysine at the 64th site is mutated into aspartic acid; aspartic acid at the 94th site is mutated into serine; cysteine at the 133rd site is mutated into threonine; phenylalanine at the 137th site is mutated into alanine;

phenylalanine at the 148th site is mutated into valine; threonine at the 173rd site is mutated into phenylalanine; arginine at the 183rd site is mutated into phenylalanine, lysine, cysteine, valine or leucine; proline at the 191st site is mutated into glutamic acid; and histidine at the 229th site is mutated into valine, alanine, glycine, serine or threonine.

Preferably, the mutation at least includes one of the following mutation sites: arginine at the 183rd site is mutated into cysteine and histidine at the 229th site is mutated into serine; arginine at the 183rd site is mutated into valine and histidine at the 229th site is mutated into serine; arginine at the 183rd site is mutated into leucine and histidine at the 229th site is mutated into alanine; threonine at the 173rd site is mutated into phenylalanine and arginine at the 183rd site is mutated into cysteine; arginine at the 183rd site is mutated into cysteine and histidine at the 229th site is mutated into leucine; arginine at the 183rd site is mutated into cysteine and tyrosine at the 207th site is mutated into arginine; arginine at the 183rd site is mutated into alanine and histidine at the 229th site is mutated into serine; arginine at the 183rd site is mutated into valine and histidine at the 229th site is mutated into asparaginate; and threonine at the 173rd site is mutated into histidine and histidine at the 229th site is mutated into serine.

Preferably, the mutation at least includes one of the following mutation sites: arginine at the 183rd site is mutated into cysteine, histidine at the 229th site is mutated into serine and phenylalanine at the 148th site is mutated into alanine; arginine at the 183rd site is mutated into cysteine, histidine at the 229th site is mutated into serine and tyrosine at the 207th site is mutated into arginine; arginine at the 183rd site is mutated into cysteine, histidine at the 229th site is mutated into serine and phenylalanine at the 148th site is mutated into valine; arginine at the 183rd site is mutated into cysteine, histidine at the 229th site is mutated into serine and threonine at the 173rd site is mutated into phenylalanine; arginine at the 183rd site is mutated into cysteine, histidine at the 229th site is mutated into serine and threonine at the 173rd site is mutated into tryptophan; arginine at the 183rd site is mutated into cysteine, histidine at the 229th site is mutated into serine and tyrosine at the 207th site is mutated into glutamic acid; arginine at the 183rd site is mutated into cysteine, histidine at the 229th site is mutated into serine and tyrosine at the 207th site is mutated into arginine; arginine at the 183rd site is mutated into alanine, histidine at the 229th site is mutated into serine and threonine at the 173rd site is mutated into histidine; arginine at the 183rd site is mutated into valine, histidine at the 229th site is mutated into serine and threonine at the 173rd site is mutated into histidine; arginine at the 183rd site is mutated into valine, histidine at the 229th site is mutated into serine and phenylalanine at the 148th site is mutated into alanine; threonine at the 173rd site is mutated into histidine, histidine at the 229th site is mutated into serine and phenylalanine at the 148th site is mutated into alanine;

or the amino acid sequence of the amino acid dehydrogenase mutant has the mutation sites in the mutated amino acid sequence, and has more than 95% homology with the mutated amino acid sequence. The term "homology" used in the present disclosure has a generally known meaning in the art. Those skilled in the art know very well rules and standards of determining the homology among different sequences. Sequences defined by the homology of different degrees must have improved amino acid dehydrogenase activity in the present disclosure.

The above amino acid dehydrogenase mutant of the present disclosure is obtained by mutating the amino acid dehydrogenase as shown in SEQ ID NO:1 through a method of site-directed mutation and through a method of directed screening, thereby changing the amino acid sequence thereof, realizing a change of protein structure and function. The amino acid dehydrogenase mutant of the present disclosure has an advantage of greatly improving enzymatic activity; the enzymatic activity is increased by over 50 times compared with that of the wild amino acid dehydrogenase; and the enzyme specificity is correspondingly increased, thereby the cost in industrial production is greatly reduced.

According to a typical embodiment of the present disclosure, lysine at the site 64 of the wild amino acid dehydrogenase is mutated into aspartic acid; aspartic acid at the 94th site is mutated into alanine, glycine, valine or serine; cysteine at the 133rd site is mutated into alanine or threonine; phenylalanine at the 137th site is mutated into alanine; phenylalanine at the 148th site is mutated into valine; asparaginate at the site 168 is mutated into aspartic acid; threonine at the 173rd site is mutated into serine, phenylalanine or leucine; arginine at the 183rd site is mutated into phenylalanine, lysine or leucine; proline at the 191st site is mutated into glutamic acid; tyrosine at the 207th site is mutated into phenylalanine or valine; histidine at the 229th site is mutated into valine, alanine, glycine, serine or threonine; serine at the 248th site is mutated into glutamic acid; asparaginate at the 255th site is mutated into alanine, glutamine or aspartic acid; and glutamine at the 282nd site is mutated into glutamic acid.

According to a typical embodiment of the present disclosure, a DNA molecule is provided. The amino acid dehydrogenase coded by the DNA is capable of improving enzymatic activity and stability of the amino acid dehydrogenase, reducing an added enzyme amount in industrial production of D-amino acids.

The above DNA molecule of the disclosure may also exist in the form of an "expression cassette". The "expression cassette" refers to a linear or circular nucleic acid molecule that encompasses DNA and RNA sequences capable of guiding expression of a specific nucleotide sequence in an appropriate host cell. Generally, including a promoter which is effectively linked with a target nucleotide, it is optionally effectively linked with a termination signal and/or other control elements. The expression cassette may also include a sequence required for proper translation of the nucleotide sequence. A coding region usually encodes a target protein, but also encodes a target function RNA in a sense or antisense direction, for example an antisense RNA or an untranslated RNA. The expression cassette including a target polynucleotide sequence may be chimeric, which means that at least one of components thereof is heterologous to at least one of the other components thereof. The expression cassette may also be existent naturally, but obtained with effective recombinant formation for heterologous expression.

According to a typical implementation of the disclosure, a recombinant plasmid is provided. The recombinant plasmid contains any one of the above DNA molecules. The DNA molecule in the above recombinant plasmid is placed in a proper position of the recombinant plasmid, so that the above DNA molecule may be correctly and smoothly copied, transcribed or expressed.

Although a qualifier used in the disclosure while the above DNA molecule is defined is "contain", it does not mean that other sequences which are not related to a function thereof may be arbitrarily added to both ends of the DNA sequence. Those skilled in the art know that in order to meet the requirements of recombination operations, it is necessary to add suitable enzyme digestion sites of a restriction enzyme at two ends of the DNA sequence, or additionally increase a start codon, a termination codon and the like, therefore, if the closed expression is used for defining, these situations may not be covered truly.

The term "plasmid" used in the disclosure includes any plasmids, cosmids, bacteriophages or *agrobacterium* binary nucleic acid molecules in double-strand or single-strand linear or circular form, preferably a recombinant expression plasmid, which may be a prokaryotic expression plasmid or may be a eukaryotic expression plasmid, preferably the prokaryotic expression plasmid, in some implementation, the recombinant expression plasmid is selected from pET-22b(+), pET-22b(+), pET-3a(+), pET-3d(+), pET-11a(+), pET-12a(+), pET-14b(+), pET-15b(+), pET-16b(+), pET-17b(+), pET-19b(+), pET-20b(+), pET-21a(+), pET-23a(+), pET-23b(+), pET-24a(+), pET-25b(+), pET-26b(+), pET-27b(+), pET-28a(+), pET-29a(+), pET-30a(+), pET-31b(+), pET-32a(+), pET-35b(+), pET-38b(+), pET-39b(+), pET-40b(+), pET-41a(+), pET-41b(+), pET-42a(+), pET-43a(+), pET-43b(+), pET-44a(+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19. More preferably, the recombinant plasmid is the pET-22b(+).

According to a typical implementation of the present disclosure, a host cell is provided. The host cell includes any one of the above recombinant plasmids. The host cell suitable for the disclosure includes, but not limited to, a prokaryotic cell, yeast or a eukaryotic cell. Preferably the prokaryotic cell is a *eubacterium*, for example a Gram-negative bacterium or a Gram-positive bacterium. More preferably the prokaryotic cell is an *Escherichia coli* BL21 cell or an *Escherichia coli* DH5a competent cell.

According to a typical implementation of the present disclosure, a method for producing D-amino acids is provided. The method includes a step of carrying out a catalytic transamination reaction on a ketone compound and an amino donor with amino acid dehydrogenase, wherein the amino acid dehydrogenase is any one of the above amino acid dehydrogenase mutants. Since the amino acid dehydrogenase mutant in the present disclosure has higher enzyme catalytic activity, the D-amino acids prepared by utilizing the amino acid dehydrogenase mutant in the present disclosure can decrease the production cost, and a value ee of the prepared D-amino acids is greater than 99%.

According to a typical embodiment of the present disclosure, the ketone compound is

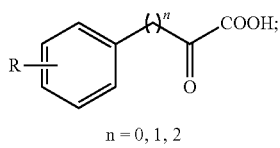

a reductive amination reaction product is

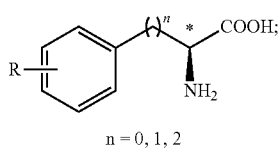

and a reaction formula is

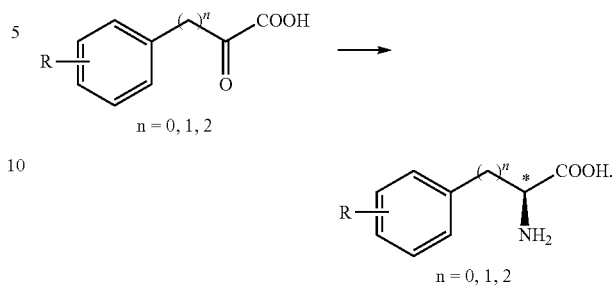

Beneficial effects of the present disclosure are further described below in combination with embodiments.

Those skilled in the art all know that, many modifications may be made to the present disclosure without departing from the spirit of the present disclosure. These modifications are included in the scope of the present disclosure. Unless otherwise specified, experimental methods below are all conventional methods; and unless otherwise specified, used experimental materials may be easily purchased from commercial corporations.

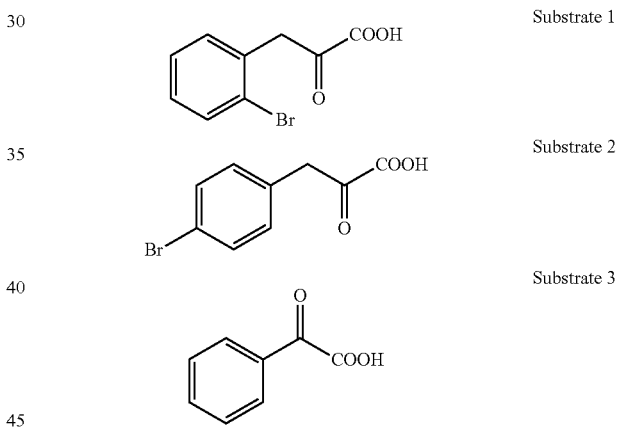

Embodiment 1

20 mg of the substrate 1 was added into 1 mL of a reaction system including 22 mg of ammonium chloride, 30 mg of glucose, 4 mg of glucose dehydrogenase, 0.4 mg of NAD$^+$, 4 mg of amino acid dehydrogenase and 0.1 M of Tris-HCl buffer; a reaction was carried out at 30° C. for 18 h; 900 μL of HCl and MeOH (0.1N HCl:MeOH=1:1) were added into 100 μL of the system; centrifugation was performed at 12000 rpm for 3 min; and the supernatant was detected. The value ee was detected as follows: 100 μL of the reaction system was taken; 100 μL of ACN, 100 μL of H$_2$O and 100 μL of 1M NaHCO$_3$ were added and then centrifuged at 12000 rpm for 3 min; the supernatant was taken out; 200 μL of 5 mg/mL Na-(2,4-binitro-5-fluorophenyl)-L-alaninamide was added and reacted at 50° C. for 1 h; 500 μL of the ACN was added for centrifugation; and the supernatant was taken for liquid chromatography.

| Substrate 1 | | |
|---|---|---|
| Enzyme | Activity | e.e. (%) |
| WT | – | 81.0 |
| K64D | + | ** |
| D94S | + | ** |
| C133T | + | ** |
| F137A | + | ** |
| F148V | ++ | *** |
| T173P | +++ | *** |
| R183P | ++ | ** |
| R183K | ++ | *** |
| R183L | ++ | *** |
| R183C | ++ | *** |
| P191E | ++ | *** |
| H229V | +++ | *** |
| H229A | +++ | *** |
| H229G | +++ | *** |
| H229S | ++ | *** |
| H229T | ++ | *** |

Compared with increase multiples of a female parent, the activity + is increased by 1-5 times; the activity ++ is increased by 5-10 times; the activity +++ is increased by 10-50 times; and the activity ++++ is increased by over 50 times.
The value ee is up to * of 80-90%; the value ee is up to  of 90-98%; and the value ee is greater than * of 98%.

Embodiment 2

20 mg of the substrate 2 was added into 1 mL of a reaction system including 22 mg of ammonium chloride, 30 mg of glucose, 4 mg of glucose dehydrogenase, 0.4 mg of $NAD^+$, 4 mg of amino acid dehydrogenase and 0.1 M of Tris-HCl buffer; a reaction was carried out at 30° C. for 18 h; 900 μL of HCl and MeOH (0.1N HCl:MeOH=1:1) were added into 100 μL of the system; centrifugation was performed at 12000 rpm for 3 min; and the supernatant was detected. The value ee was detected as follows: 100 μL of the reaction system was taken; 100 μL of ACN, 100 μL of $H_2O$ and 100 μL of 1M $NaHCO_3$ were added and then centrifuged at 12000 rpm for 3 min; the supernatant was taken out; 200 μL of 5 mg/mL Na-(2,4-binitro-5-fluorophenyl)-L-alaninamide was added and reacted at 50° C. for 1 h; 500 μL of the ACN was added for centrifugation; and the supernatant was taken for liquid chromatography.

| Substrate 2 | | |
|---|---|---|
| Enzyme | Activity | e.e. (%) |
| WT | – | 88.4 |
| K64D | + | ** |
| D94S | + | ** |
| C133T | + | ** |
| F137A | + | ** |
| F148V | ++ | *** |
| T173P | ++ | *** |
| R183P | ++ | *** |
| R183K | + | *** |
| R183L | +++ | *** |
| R183C | +++ | *** |
| P191E | ++ | *** |
| H229V | ++ | *** |
| H229A | +++ | *** |
| H229G | ++ | *** |
| H229S | ++ | *** |
| H229T | ++ | *** |

Compared with increase multiples of a female parent, the activity + is increased by 1-5 times; the activity ++ is increased by 5-10 times; the activity +++ is increased by 10-50 times; and the activity ++++ is increased by over 50 times.
The value ee is up to * of 80-90%; the value ee is up to  of 90-98%; and the value ee is greater than * of 98%.

Embodiment 3

20 mg of the substrate 3 was added into 1 mL of a reaction system including 22 mg of ammonium chloride, 30 mg of glucose, 4 mg of glucose dehydrogenase, 0.4 mg of $NAD^+$, 4 mg of amino acid dehydrogenase and 0.1 M of Tris-HCl buffer; a reaction was carried out at 30° C. for 18 h; 900 μL of HCl and MeOH (0.1N HCl:MeOH=1:1) were added into 100 μL of the system; centrifugation was performed at 12000 rpm for 3 min; and the supernatant was detected. The value ee was detected as follows: 100 μL of the reaction system was taken; 100 μL of ACN, 100 μL of $H_2O$ and 100 μL of 1M $NaHCO_3$ were added and then centrifuged at 12000 rpm for 3 min; the supernatant was taken out; 200 μL of 5 mg/mL Na-(2,4-binitro-5-fluorophenyl)-L-alaninamide was added and reacted at 50° C. for 1 h; 500 μL of the ACN was added for centrifugation; and the supernatant was taken for liquid chromatography.

| Substrate 3 | | |
|---|---|---|
| Enzyme | Activity | e.e. (%) |
| WT | – | 71.1 |
| K64D | + | * |
| D94S | + | * |
| C133T | + | * |
| F137A | + | * |
| F148V | + | * |
| T173P | ++ | * |
| R183P | + | * |
| R183K | + | * |
| R183L | ++ | * |
| R183C | ++ | * |
| P191E | ++ | * |
| H229V | + | * |
| H229A | + | * |
| H229G | + | * |
| H229S | ++ | * |
| H229N | ++ | * |

Compared with increase multiples of a female parent, the activity + is increased by 1-5 times; the activity ++ is increased by 5-10 times; the activity +++ is increased by 10-50 times; and the activity ++++ is increased by over 50 times.
The value ee is up to * of 80-90%; the value ee is up to  of 90-98%; and the value ee is greater than * of 98%.

Mutation is continuously performed, thereby increasing a substrate concentration and decreasing a reaction volume.

Embodiment 4

33 mg of the substrate 1 was added into 1 mL of a reaction system, 33 mg of ammonium chloride, 49.5 mg of glucose, 6.6 mg of glucose dehydrogenase, 0.66 mg of $NAD^+$, 6.6 mg of amino acid dehydrogenase and 0.1 M of Tris-HCl buffer; a reaction was carried out at 30° C. for 18 h; 900 μL of HCl and MeOH (0.1N HCl:MeOH=1:1) were added into 100 μL of the system; centrifugation was performed at 12000 rpm for 3 min; and the supernatant was detected. The value ee was detected as follows: 100 μL of the reaction system was taken; 100 μL of ACN, 100 μL of $H_2O$ and 100 μL of 1M $NaHCO_3$ were added and then centrifuged at 12000 rpm for 3 min; the supernatant was taken out; 200 μL of 5 mg/mL Na-(2,4-binitro-5-fluorophenyl)-L-alaninamide was added and reacted at 50° C. for 1 h; 500 μL of the ACN was added for centrifugation; and the supernatant was taken for liquid chromatography.

| | Substrate 1 | |
|---|---|---|
| Enzyme | Activity | e.e. (%) |
| R183C + H229S | +++ | *** |
| R183V + H229S | +++ | *** |
| T173H + R183C | ++ | *** |
| R183L + H229A | +++ | *** |
| H229L + R183C | +++ | *** |
| Y207R + R183C | +++ | *** |

Compared with increase multiples of a female parent, the activity + is increased by 1-5 times; the activity ++ is increased by 5-10 times; the activity +++ is increased by 10-50 times; and the activity ++++ is increased by over 50 times.
The value ee is up to * of 80-90%; the value ee is up to  of 90-98%; and the value ee is greater than * of 98%.

Embodiment 5

33 mg of the substrate 2 was added into 1 mL of a reaction system including 33 mg of ammonium chloride, 49.5 mg of glucose, 6.6 mg of glucose dehydrogenase, 0.66 mg of NAD⁺, 6.6 mg of amino acid dehydrogenase and 0.1 M of Tris-HCl buffer; a reaction was carried out at 30° C. for 18 h; 900 µL of HCl and MeOH (0.1N HCl:MeOH=1:1) were added into 100 µL of the system; centrifugation was performed at 12000 rpm for 3 min; and the supernatant was detected. The value ee was detected as follows: 100 µL of the reaction system was taken; 100 µL of ACN, 100 µL of H₂O and 100 µL of 1M NaHCO₃ were added and then centrifuged at 12000 rpm for 3 min; the supernatant was taken out; 200 µL of 5 mg/mL Na-(2,4-binitro-5-fluorophenyl)-L-alaninamide was added and reacted at 50° C. for 1 h; 500 µL of the ACN was added for centrifugation; and the supernatant was taken for liquid chromatography.

| | Substrate 2 | |
|---|---|---|
| Enzyme | Activity | e.e. (%) |
| R183C + H229S | +++ | *** |
| R183V +H229S | +++ | *** |
| T173H + R183C | ++ | *** |
| R183L + H229S | +++ | *** |
| H229L + R183C | +++ | *** |
| Y207R + R183C | ++ | *** |

Compared with increase multiples of a female parent, the activity + is increased by 1-5 times; the activity ++ is increased by 5-10 times; the activity +++ is increased by 10-50 times; and the activity ++++ is increased by over 50 times.
The value ee is up to * of 80-90%; the value ee is up to  of 90-98%; and the value ee is greater than * of 98%.

Embodiment 6

33 mg of the substrate 3 was added into 1 mL of a reaction system including 33 mg of ammonium chloride, 49.5 mg of glucose, 6.6 mg of glucose dehydrogenase, 0.66 mg of NAD⁺, 6.6 mg of amino acid dehydrogenase and 0.1 M of Tris-HCl buffer; a reaction was carried out at 30° C. for 18 h; 900 µL of HCl and MeOH (0.1N HCl:MeOH=1:1) were added into 100 µL of the system; centrifugation was performed at 12000 rpm for 3 min; and the supernatant was detected. The value ee was detected as follows: 100 µL of the reaction system was taken; 100 µL of ACN, 100 µL of H₂O and 100 µL of 1M NaHCO₃ were added and then centrifuged at 12000 rpm for 3 min; the supernatant was taken out; 200 µL of 5 mg/mL Na-(2,4-binitro-5-fluorophenyl)-L-alaninamide was added and reacted at 50° C. for 1 h; 500 µL of the ACN was added for centrifugation; and the supernatant was taken for liquid chromatography.

| | Substrate 3 | |
|---|---|---|
| Enzyme | Activity | e.e. (%) |
| R183C + H229S | ++ | * |
| R183A + H229S | ++ | *** |
| R183V + H229S | ++ | ** |
| R183V + H229N | ++ | *** |
| T173H + H229S | ++ | *** |

Compared with increase multiples of a female parent, the activity + is increased by 1-5 times; the activity ++ is increased by 5-10 times; the activity +++ is increased by 10-50 times; and the activity ++++ is increased by over 50 times.
The value ee is up to * of 80-90%; the value ee is up to  of 90-98%; and the value ee is greater than * of 98%.

Beneficial mutation sites were further combined, thereby further increasing the substrate concentration and decreasing the reaction volume.

Embodiment 7

50 mg of the substrate 1 was added into 1 mL of a reaction system including 55 mg of ammonium chloride, 75 mg of glucose, 10 mg of glucose dehydrogenase, 1 mg of NAD⁺, 10 mg of amino acid dehydrogenase and 0.1 M of Tris-HCl buffer; a reaction was carried out at 30° C. for 18 h; 900 µL of HCl and MeOH (0.1N HCl:MeOH=1:1) were added into 100 µL of the system; centrifugation was performed at 12000 rpm for 3 min; and the supernatant was detected. The value ee was detected as follows: 100 µL of the reaction system was taken; 100 µL of ACN, 100 µL of H₂O and 100 µL of 1M NaHCO₃ were added and then centrifuged at 12000 rpm for 3 min; the supernatant was taken out; 200 µL of 5 mg/mL Na-(2,4-binitro-5-fluorophenyl)-L-alaninamide was added and reacted at 50° C. for 1 h; 500 µL of the ACN was added for centrifugation; and the supernatant was taken for liquid chromatography.

| | Substrate 1 | |
|---|---|---|
| Enzyme | Activity | e.e. (%) |
| R183C + H229S + F148A | ++++ | *** |
| R183C + H229S + Y207R | ++++ | *** |
| R183C + H229S + F148V | +++ | *** |
| R183C + H229S + T173F | +++ | *** |
| R183C + H229S + T173W | +++ | *** |
| R183C + H229S + Y207E | ++++ | *** |

Compared with increase multiples of a female parent, the activity + is increased by 1-5 times; the activity ++ is increased by 5-10 times; the activity +++ is increased by 10-50 times; and the activity ++++ is increased by over 50 times.
The value ee is up to * of 80-90%; the value ee is up to  of 90-98%; and the value ee is greater than * of 98%.

Embodiment 8

50 mg of the substrate 2 was added into 1 mL of a reaction system including 55 mg of ammonium chloride, 75 mg of glucose, 10 mg of glucose dehydrogenase, 1 mg of NAD⁺, 10 mg of amino acid dehydrogenase and 0.1 M of Tris-HCl buffer; a reaction was carried out at 30° C. for 18 h; 900 µL of HCl and MeOH (0.1N HCl:MeOH=1:1) were added into 100 µL of the system; centrifugation was performed at 12000 rpm for 3 min; and the supernatant was detected. The value ee was detected as follows: 100 µL of the reaction system was taken; 100 µL of ACN, 100 µL of H₂O and 100 µL of 1M NaHCO₃ were added and then centrifuged at 12000 rpm for 3 min; the supernatant was taken out; 200 µL of 5 mg/mL Na-(2,4-binitro-5-fluorophenyl)-L-alaninamide was added and reacted at 50° C. for 1 h; 500 μL of the ACN was added for centrifugation; and the supernatant was taken for liquid chromatography.

| Enzyme | Substrate 2 | |
|---|---|---|
| | Activity | e.e. (%) |
| R183C + H229S + F148A | ++++ | *** |
| R183C + H229S + F148V | +++ | *** |
| R183C + H229S + T173F | +++ | *** |
| R183C + H229S + T173W | +++ | *** |
| R183C + H229S + Y207E | ++++ | *** |
| R183C + H229S + Y207R | ++++ | *** |

Compared with increase multiples of a female parent, the activity + is increased by 1-5 times; the activity ++ is increased by 5-10 times; the activity +++ is increased by 10-50 times; and the activity ++++ is increased by over 50 times.
The value ee is up to * of 80-90%; the value ee is up to  of 90-98%; and the value ee is greater than * of 98%.

Embodiment 9

50 mg of the substrate 3 was added into 1 mL of a reaction system including 55 mg of ammonium chloride, 75 mg of glucose, 10 mg of glucose dehydrogenase, 1 mg of NAD$^+$, 10 mg of amino acid dehydrogenase and 0.1 M of Tris-HCl buffer; a reaction was carried out at 30° C. for 18 h; 900 μL of HCl and MeOH (0.1N HCl:MeOH=1:1) were added into 100 μL of the system; centrifugation was performed at 12000 rpm for 3 min; and the supernatant was detected. The value ee was detected as follows: 100 μL of the reaction system was taken; 100 μL of ACN, 100 μL of H$_2$O and 100 μL of 1M NaHCO$_3$ were added and then centrifuged at 12000 rpm for 3 min; the supernatant was taken out; 200 μL of 5 mg/mL Na-(2,4-binitro-5-fluorophenyl)-L-alaninamide was added and reacted at 50° C. for 1 h; 500 μL of the ACN was added for centrifugation; and the supernatant was taken for liquid chromatography.

| Enzyme | Substrate 3 | |
|---|---|---|
| | Activity | e.e. (%) |
| R183A + H229S + T173H | ++++ | *** |
| R183V + H229S + T173H | ++++ | *** |
| R183V + H229S + F148A | ++++ | *** |
| T173H + H229S + F148A | ++++ | *** |

Compared with increase multiples of a female parent, the activity + is increased by 1-5 times; the activity ++ is increased by 5-10 times; the activity +++ is increased by 10-50 times; and the activity ++++ is increased by over 50 times.
The value ee is up to * of 80-90%; the value ee is up to  of 90-98%; and the value ee is greater than * of 98%.

The above only describes the preferred embodiments of the present disclosure and not intended to limit the present disclosure. For those skilled in the art, various modifications and changes can be made to the present disclosure. Any modification, equivalent substitution and improvement made within the spirit and principle of the present disclosure shall be included within the protection scope of the present disclosure.

What is claimed is:

1. An amino acid dehydrogenase mutant, wherein the amino acid sequence of the mutant is obtained by mutating the amino acid sequence shown in SEQ ID NO:1; the mutation comprises one of the following mutation site combinations:

arginine at the 183rd site is mutated into cysteine, histidine at the 229th site is mutated into serine and phenylalanine at the 148th site is mutated into alanine;

arginine at the 183rd site is mutated into cysteine, histidine at the 229th site is mutated into serine and tyrosine at the 207th site is mutated into arginine;

arginine at the 183rd site is mutated into cysteine, histidine at the 229th site is mutated into serine and tyrosine at the 207th site is mutated into glutamic acid;

arginine at the 183rd site is mutated into alanine, histidine at the 229th site is mutated into serine and threonine at the 173rd site is mutated into histidine;

arginine at the 183rd site is mutated into valine, histidine at the 229th site is mutated into serine and threonine at the 173rd site is mutated into histidine;

arginine at the 183rd site is mutated into valine, histidine at the 229th site is mutated into serine and phenylalanine at the 148th site is mutated into alanine;

threonine at the 173rd site is mutated into histidine, histidine at the 229th site is mutated into serine and phenylalanine at the 148th site is mutated into alanine.

* * * * *